United States Patent
Capelle et al.

[11] Patent Number: 6,093,317
[45] Date of Patent: Jul. 25, 2000

[54] DEVICE FOR DISCONTINUOUS INJECTION OF A FLUID F2 INTO A ZONE Z1 OR DISCONTINUOUS EXTRACTION OF A FLUID F1 FROM A ZONE Z1

[75] Inventors: Marianne Capelle, Ternay; Roland Huin, Sainte Foy les Lyon, both of France

[73] Assignee: Institut Francais du Petrole, Cedex, France

[21] Appl. No.: 09/241,855

[22] Filed: Feb. 2, 1999

[30] Foreign Application Priority Data

Feb. 2, 1998 [FR] France .................................. 98-01272

[51] Int. Cl.[7] .................................................. B01D 15/08
[52] U.S. Cl. ............................ 210/198.2; 210/659; 96/107
[58] Field of Search ........................... 210/656, 659, 210/198.2, 283, 284, 289, 285, 291, 541; 96/107

[56] References Cited

U.S. PATENT DOCUMENTS

| | | | |
|---|---|---|---|
| 2,985,589 | 5/1961 | Broughton et al. | 210/34 |
| 3,214,247 | 10/1965 | Broughton | 210/198.2 |
| 5,846,411 | 12/1998 | Harter | 210/198.2 |
| 6,024,871 | 2/2000 | Harter | 210/198.2 |

FOREIGN PATENT DOCUMENTS

| | | | |
|---|---|---|---|
| 0 581 153 | 2/1994 | European Pat. Off. | 210/198.2 |
| 7 722 355 | 3/1999 | European Pat. Off. | 210/198.2 |
| 95/03867 | 9/1995 | WIPO | 210/198.2 |

*Primary Examiner*—Ernest G. Therkorn
*Attorney, Agent, or Firm*—Millen, White, Zelano & Branigan, P.C.

[57] ABSTRACT

Injection or extraction device that comprises at least one injection or extraction rail 2 that is integral with a chamber 1 for injecting a fluid F2 into a zone Z1 or for extracting a fluid F1 from zone Z1 in which said fluid circulates, whereby the rail comprises at least one orifice 3 that makes it possible for fluid F2 to pass into zone Z1 or for said fluid F1 to be extracted from zone Z1 and that in front of each orifice comprises at least one means 5 for at least partial blocking of the orifice, whereby the means is located downstream or upstream from the rail in the direction of circulation of fluid F2 and that makes it possible for fluid F2 to pass into zone Z1 or for said fluid F1 to be extracted from zone Z1. Use of the device for monitoring the injection or extraction of a first fluid in the simultaneous presence of a second fluid that is different from the first fluid.

13 Claims, 1 Drawing Sheet

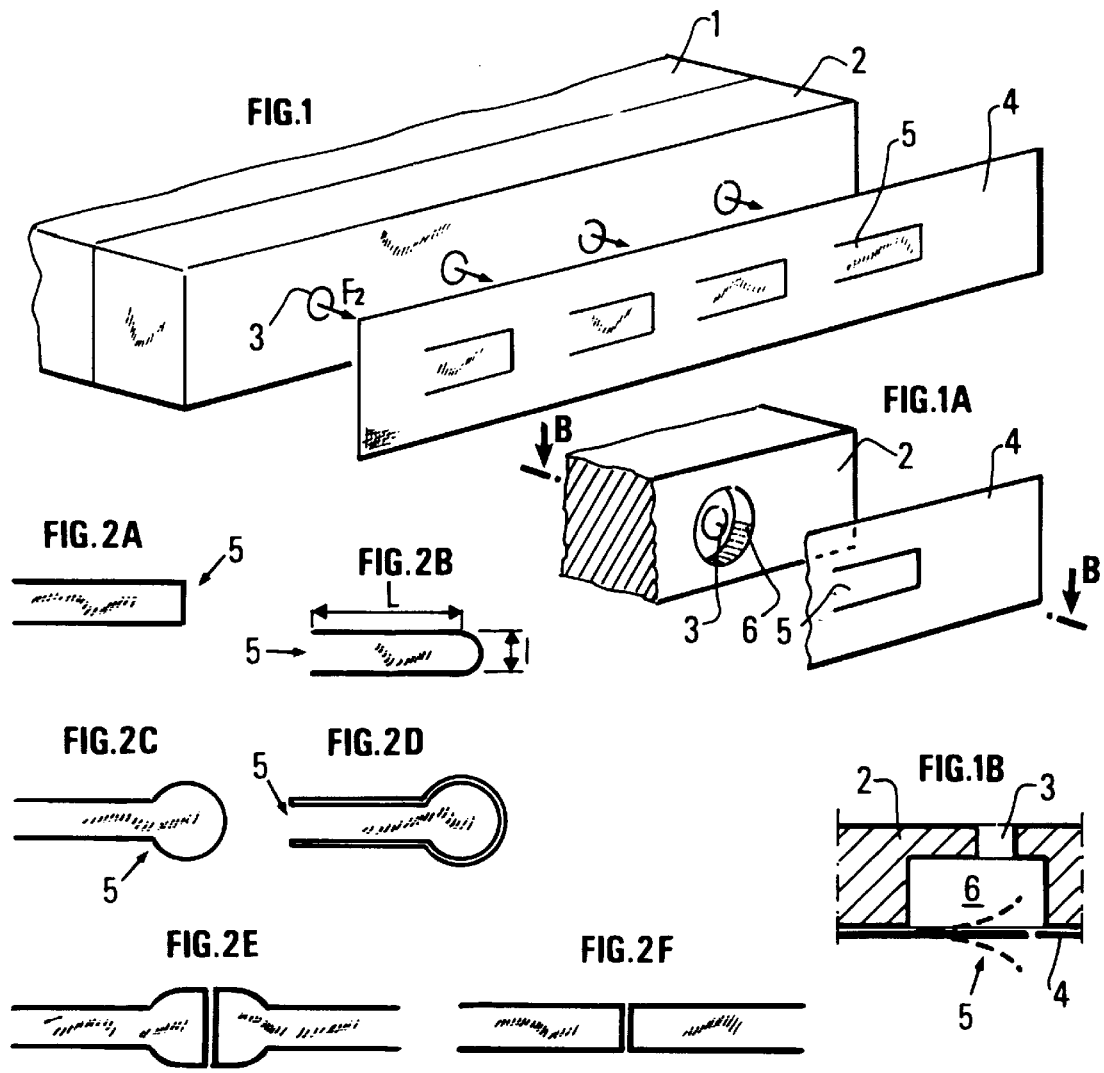
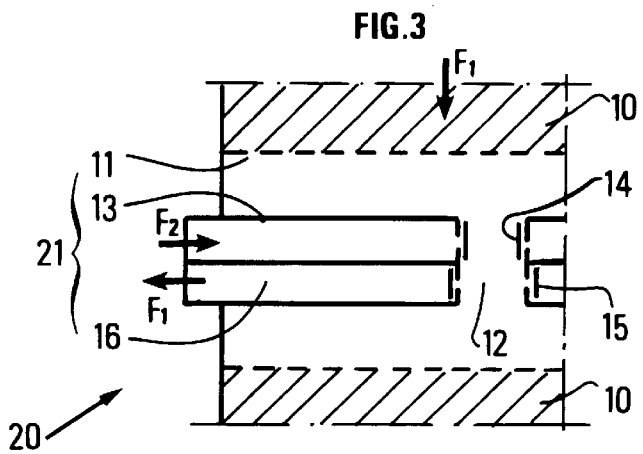

DEVICE FOR DISCONTINUOUS INJECTION OF A FLUID F2 INTO A ZONE Z1 OR DISCONTINUOUS EXTRACTION OF A FLUID F1 FROM A ZONE Z1

This invention relates to the field of chromatography and more particularly to that of simulated fluid bed chromatography for the purification of a given product or for the separation of a product that is contained in a mixture.

The prior art is illustrated by Patent EP-A-581 153, which describes a filter that comprises flexible metal loops that determine the slots for the passage of liquids that can be cleaned easily.

In chromatography processes, a molecular sieve is used on which the compounds of the mixture are adsorbed and are then eluted using a solvent. In particular in the case of simulated fluid bed chromatography, often with simulated counter-current, most often large diameters of columns and numerous separation stages are linked to periodic injection or draw-off of products between two stages. U.S. Pat. No. 3,214,247 describes, for example, a chromatography column that comprises a number of stages in which all of the main fluid is collected downstream from a collecting lattice that is positioned at the outlet of a first bed and said fluid is redistributed downstream from a lattice that is located close to a second bed. The secondary fluid is introduced through holes that are positioned in the central zone of the collecting zone, where it mixes directly with the main fluid. This system offers the advantage of having small dead volumes and of inducing a pressure drop that is relatively mild because of its transverse collection. Nevertheless, the mixing function has not been completely mastered and, in particular, can induce back-mixing phenomena in the entire conical collecting and/or redistribution section. Moreover, it is certain that when the secondary fluid is halted, the main fluid can enter through the holes in the means that are used for introducing or extracting the secondary fluid, which will contaminate a fraction of said secondary fluid during its reintroduction or reextraction in a later phase.

U.S. Pat. No. 2,985,589 describes a continuous chromatography adsorption process that uses fixed beds of adsorbents and so-called mobile inlets and outlets for the various phases that are formed by the feedstock, the solvent or displacement agent, the raffinate and the extract. The control valves thus make it possible to introduce the solvent or the feedstock successively and periodically into each of the adsorption beds and to extract an extract and a raffinate from each of these beds. These successive phases of introduction to and extraction from the various beds that use the same pipe produce contamination of the product that is extracted from or introduced into a bed by the product that is extracted from or introduced into the same bed in the preceding phase. Furthermore, in this embodiment, the main fluid can at any time contaminate in the pipe the product that is extracted or that is introduced during the phase during which said introduction or said extraction is halted. Thus, this system generally does not make it possible to obtain a satisfactory purity for the desired product.

Most often, as is described in, for example, the European patent application in the name of the applicant EP-A-722355, each adsorbent bed is separated from the next by a system that is referred to as a distributor-mixer-extractor which comprises a means for introducing a secondary fluid into the main fluid. This system, as it is described in this application, comprises a pipe for introducing the secondary fluid into an injection chamber and then into a mixing chamber into which the main fluid also enters and, downstream from this mixing chamber in the direction of circulation of the main fluid, a means for redistributing the mixture that is formed. In this implementation, when the introduction of the secondary fluid is halted, only the pressure that comes from the secondary fluid column height opposes the reflux of the main fluid in the pipe for introducing the secondary fluid. Thus, the secondary fluid remains in contact with the main fluid, and the pressure of said secondary fluid is insufficient to effectively oppose the contamination of this secondary fluid by the main fluid.

This invention mitigates the above-mentioned drawbacks and aims at avoiding or at least greatly limiting the contamination risks of the products that are introduced or extracted, in particular by the main fluid, during the phase in which nothing is introduced into the injection chamber and nothing more is extracted in the extraction chamber. The invention relates to a device that makes it possible to periodically inject a fluid F2 into a zone Z1 in which a fluid F1 circulates or to periodically extract fluid F1 from this zone Z1.

In its broadest form, this invention relates to an injection or extraction device that comprises at least one injection or extraction rail that is integral with a chamber for injecting a fluid F2 into a zone Z1 or for extracting a fluid F1 from zone Z1 in which this fluid circulates, whereby said rail comprises at least one or, preferably, more orifices that make it possible for said fluid F2 to pass into zone Z1 or for said fluid F1 to be extracted from zone Z1, characterized in that in front of each orifice, it comprises at least one means for at least partial blocking of said orifice, whereby said means is located downstream or upstream from said rail in the direction of circulation of said fluid F2 and that makes it possible for fluid F2 to pass into said zone Z1 or for fluid F1 to be extracted from said zone Z1 in the extraction chamber.

One of the advantages of this device is that it at least partially prevents the mixing of these two fluids when the injection of fluid F2 is halted or the extraction of fluid F1 is halted.

In a preferred embodiment of this invention, said means for at least partial blocking of each orifice comprises a spring blade that is integral with or is made integral with the injection rail that comprises a cutout, the part of which that is located opposite each orifice of said injection or extraction rail opens or half-opens under the action of the pressure that is exerted by fluid F2, in such a way as to allow this fluid F2 to pass into zone Z1 or to allow fluid F1 to pass from zone Z1 into the extraction chamber. The cutout of this spring blade most often strikes the rail when the flow of fluid F2 stops or when the extraction of fluid F1 stops.

According to a particular embodiment, it is possible to have a blocking means that is formed by two spring blades that work with one another in closing the orifice. In the preferred embodiment of the invention in which the rail comprises a number of orifices, a single spring blade that is made integral with the rail and that comprises as many cutouts as there are rail orifices will be used. Another embodiment of the invention applies to a device which, at rest, blocks the circuit that is able to retract under the action of a certain pressure that was previously known.

Although various materials can be used that in particular exhibit elasticity characteristics that are selected based on operating conditions, most often a spring blade that is made of an elastic metal will be used. The blade will be made of, for example, carbon steel, stainless steel, or any other metal that has the elasticity that is desired for performing its function under the working conditions. The selection of a suitable material by one skilled in the art should take into account the operating conditions, in particular the number of injection or extraction cycles that it is desired to ensure, the working pressure, the temperatures and compositions of the various fluids with which the blade enters into contact, and in particular the risks of corrosion of the metal by the fluids that are used. This selection is a relatively easy choice for one skilled in the art and is broadly guided by basic works or by the description of physical characteristics and mechanical properties that are provided by the vendor of metal spring blades. The thickness of the blade is usually about 0.01 millimeter (mm) to about 1.5 mm, often from about 0.02 to about 1 mm, and most often from about 0.05 mm to about 0.6 mm. The framework of this invention will not be exceeded if a means is used that makes it possible to exert a force or a minimum pressure to open it. Such a means can be, for example, a particular form of the blade, a shaping of blades, or a related elastic device that makes it possible to use prestressing which allows it to open only under the application of a known minimum effort.

The spring blade can be made integral with the rail by any means that is well known to one skilled in the art. It can be glued, screwed, clamped, gripped, or welded. Most often, it will be screwed or welded. The cutouts that this blade comprises are generally made before it is made integral with the rail. They usually have a shape that is adapted to the function that they are to perform in connection with the shapes of the orifices.

It is possible to have different cutout shapes for the same orifice shape. Most often, all of the cutouts of the same blade have the same shape as all of the orifices of the same rail. The framework of this invention will not be exceeded, however, if a rail is used that has orifices of different shapes and/or a blade that has cutouts of different shapes. The direction of the cutout is usually selected based on the direction of the flow of fluid F1. This selection results from the function that this cutout performs, which is to oppose the passage of fluid F1 into the fluid injection or extraction chamber when the injection or extraction of this fluid is halted. Thus, although this is not an absolute necessity, the cutout will very often be made in the same direction as that in which fluid F1 circulates.

Within the framework of this invention, fluids F1 and F2 can circulate in cross-current, in co-current, or in counter-current.

Various other features and attendant advantages of the present invention will be more fully appreciated as the same becomes better understood when considered in conjunction with the accompanying drawings, in which like reference characters designate the same or similar parts throughout the several views, and wherein:

BRIEF DESCRIPTION OF THE DRAWINGS

The invention will be better understood based on the following figures:

FIG. 1 diagrammatically depicts in exploded view the device of the invention, and FIGS. 1a and 1b show a variant, FIGS. 2a, 2b, 2c and 2d show the shape that a simple cutout can have, and FIGS. 2e and 2f show the shape that a double-blade cutout with a symmetrical opening can have, FIG. 3 diagrammatically depicts a chromatography column that comprises the device according to the invention.

DESCRIPTION OF THE PREFERRED EMBODIMENTS

According to FIG. 1, chamber 1 for injecting or extracting fluid F2 comprises a rail 2 that comprises a number of orifices 3 that are approximately circular, and spring blade 4 comprises a number of cutouts 5 that are sized and positioned in such a way that the end of each cutout entirely covers an orifice and is laid on the rail when the circulation of fluid F2, for example, is halted. This diagrammatization should not be regarded as a limitation of this invention. FIG. 1a shows a diagram of another embodiment of the invention, and this shape is seen in section along axis BB in FIG. 1b. The reference numbers and letters refer to the same elements in each of the figures. In said FIGS. 1a and 1b, rail 2 comprises an orifice 3 that forms a chamber 6 that is large enough that cutout 5 in spring blade 4 is also able to open toward the inside of this chamber.

FIG. 3 diagrammatically shows the use of the device of this invention in a chromatography column 20 that comprises a number of adsorption stages 10 on a solid (molecular sieve, for example) that are separated by distributor plates 21. Diagrammed in this figure is a single fluid distributor plate that comprises two devices according to the invention, one that allows the injection of a fluid F2 from the outside into the column and the other that allows the extraction of a fluid F1 from the column toward the outside. This figure should not be regarded as limiting. Fluid F1 passes through adsorbent solid 10 that is supported by a lattice 11 of the plate and enters into space 12 into which, during a stage, for a given period, fluid F2 is introduced by supply chamber 13 that is equipped with device 14 according to the invention, diagrammed here by a double line, or in another stage, fluid F1 is extracted for a given period by use of device 15 according to the invention and extraction chamber 16. In the column, the composition of fluid F1 varies from one stage to the next and varies as a function of the injection cycles of the solvent and the feedstock, and the extraction of the raffinate and the extract.

Most often, separate chambers are used for the injection of fluid F2 and for the extraction of fluid F1. In a particular embodiment of this invention, however, one and the same chamber can be used for the injection of fluid F2 and then for the extraction of fluid F1. In the latter case, it is possible to use a rail 2 that comprises a larger number of orifices 3, on which is made integral from each side a blade 4 that alternately comprises at least one means 5 for at least partial blocking of an orifice of the rail and at least one orifice that is placed opposite another orifice of the rail, whereby said blade is located downstream from said rail in the direction of circulation of the fluid and makes it possible for fluid F2 to pass into zone Z1 via certain orifices and for fluid F1 to be extracted from zone Z1 using other orifices.

To do this, the orifices of the upstream and downstream blades are shifted in such a way that the orifice of one blade coincides with the blocking means of the other blade.

The device of this invention finds application in all cases of chemical engineering that require that the injection or extraction of a first fluid be monitored in the simultaneous presence of a second fluid that is different from said first fluid.

This invention relates in particular to the use of the device for obtaining at least one isomer of xylene from a hydrocarbon fraction that contains aromatic compounds with 8 carbon atoms, including the desired xylene isomer. This separation is done by chromatography and most often by so-called simulated cross-current chromatography.

The following examples illustrate the invention without limiting its scope.

COMPARATIVE EXAMPLE

We use liquid hexane as injection fluid F2 and liquid heptane as main fluid F1. The pressure of the unit is 0.15

Mpa, and the temperature is 20° C. An injection chamber uses an injection rail that comprises eight orifices 5 mm in diameter. In injection, the hexane circulates at 10 m/s in each orifice. The heptane circulates continuously in cross-current with hexane, at a speed of 50 cm/s in front of the orifices.

The injection of hexane lasts for 5 mm and is then halted. At the end of injection, the injection chamber is filled with hexane. A refractometer probe is installed in the chamber for measuring the heptane concentration as a function of time. The latter, which is zero at the end of injection, changes with time up to a maximum value. From this measurement the heptane circulation flow in the chamber is deduced. It is 20 l/h in this test.

EXAMPLE ACCORDING TO THE INVENTION

The example above is repeated, but a stainless steel spring blade is welded onto the rail. It has a thickness of 0.2 mm and comprises eight semi-oblong cutouts, as diagrammed in FIG. 2b. Each cutout is located in front of an orifice of the rail. Length L of the cutout is 15 mm, and its width 1 to 7 mm. The pressure drop that is introduced by the device is 0.02 Mpa during hexane injection. When the introduction of hexane is halted, the cutout piece of the blade lies flat on the rail, which greatly limits the passage of the main fluid into the injection chamber. As a function of time, the heptane concentration in the chamber is measured as above from the moment when the hexane is halted. The heptane circulation flow rate in the chamber when injection is halted is estimated at 2 l/h from these measurements. The hexane chamber is therefore much less contaminated with heptane than in the preceding case.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above, and of French priority application 98/01.272, filed Feb. 2, 1998, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A simulated moving bed device for discontinuous injection or discontinuous extraction of a fluid that is used for the monitoring of said injection or said extraction that comprises at least one injection or extraction rail (2) that is integral with a chamber (1) for injecting a fluid F2 into a zone Z1 or for extracting a fluid F1 from zone Z1 in which this fluid circulates, whereby said rail comprises at least one orifice (3) that makes it possible for said fluid F2 to pass into zone Z1 or for fluid F1 to be extracted from zone Z1, characterized in that in front of each orifice, it comprises at least one means (4) (5) for at least partial blocking of said orifice, whereby said means is located downstream or upstream from said rail in the direction of circulation of said fluid F2 and that makes it possible for fluid F2 to pass into said zone Z1 or for fluid F1 to be extracted from said zone Z1 in the extraction chamber.

2. Device according to claim 1, wherein the means for at least partial blocking of each orifice of the rail comprises a spring blade that is integral with or is made integral with the injection rail that comprises a cutout whose part that is located opposite each orifice of said injection or extraction rail opens or half-opens under the action of the pressure that is exerted by fluid F2, in such a way as to allow said fluid F2 to pass into zone Z1 or under the action of the pressure that is exerted by fluid F1, in such a way as to allow this fluid F1 to pass from zone Z1 into the extraction chamber.

3. Device according to claim 2, wherein the rail comprises a number of orifices and in which the means for at least partial blocking of each orifice of the rail is a single spring blade that is made integral with the rail and that comprises as many cutouts as there are orifices in the rail.

4. Device according to claim 3, wherein the spring blade is an elastic metal blade.

5. Device according to claim 4, wherein the spring blade is a carbon steel blade or stainless steel blade.

6. Device according to claim 5, wherein the spring blade has a thickness of about 0.01 millimeter (mm) to about 1.5 mm.

7. Device according to claim 6, wherein the blocking means comprises at least one means that makes it possible to exert a minimum force or pressure to open it.

8. Device according to claim 7, wherein the rail comprises orifices and wherein a blade is made integral with each side of the rail and alternately comprises at least one means for at least partial blocking of an orifice of the rail and at least one orifice that is placed opposite another orifice of the rail, whereby said blade is located downstream from the rail in the direction of circulation of the fluid and that makes it possible for fluid F2 to pass into zone Z1 by use of certain orifices and for fluid F1 to be extracted from zone Z1 using other orifices, whereby the orifices of the upstream and downstream blades are shifted in such a way that the orifice of one blade coincides with the blocking means of the other blade.

9. Device according to claim 1, wherein the rail comprises a number of orifices and in which the means for at least partial blocking of each orifice of the rail is a single spring blade that is made integral with the rail and that comprises as many cutouts as there are orifices in the rail.

10. Device according to claim 1, wherein the spring blade is an elastic metal blade.

11. Device according to claim 1, wherein the spring blade has a thickness of about 0.01 mm to about 1.5 mm.

12. Device according to claim 1, wherein the blocking means comprises at least one means that makes it possible to exert a minimum force or pressure to open it.

13. Device according to claim 1, wherein the rail comprises orifices and wherein a blade is made integral with each side of the rail and alternately comprises at least one means for at least partial blocking of an orifice of the rail and at least one orifice that is placed opposite another orifice of the rail, whereby said blade is located downstream from the rail in the direction of circulation of the fluid and that makes it possible for fluid F2 to pass into zone Z1 by use of certain orifices and for fluid F1 to be extracted from zone Z1 using other orifices, whereby the orifices of the upstream and downstream blades are shifted in such a way that the orifice of one blade coincides with the blocking means of the other blade.

* * * * *